United States Patent [19]
Mollenauer

[11] Patent Number: 5,797,947
[45] Date of Patent: *Aug. 25, 1998

[54] METHODS AND DEVICES FOR HARVESTING BLOOD VESSELS WITH BALLOONS

[75] Inventor: Kenneth H. Mollenauer, Santa Clara, Calif.

[73] Assignee: General Surgical Innovations, Inc., Cupertino, Calif.

[*] Notice: This patent issued on a continued prosecution application filed under 37 CFR 1.53(d), and is subject to the twenty year patent term provisions of 35 U.S.C. 154(a)(2).

[21] Appl. No.: 781,219

[22] Filed: Jan. 10, 1997

Related U.S. Application Data

[63] Continuation of Ser. No. 444,426, May 19, 1995, Pat. No. 5,593,418.

[51] Int. Cl.⁶ ........................................... A61M 29/00
[52] U.S. Cl. ........................ 606/192; 606/108; 606/194
[58] Field of Search ........................ 606/192, 194, 606/198

[56] References Cited

U.S. PATENT DOCUMENTS

| | | | |
|---|---|---|---|
| 5,314,443 | 5/1994 | Rudnick | 606/192 |
| 5,593,418 | 1/1997 | Mollenauer | 606/192 |
| 5,601,589 | 2/1997 | Fogarty et al. | 606/192 |

*Primary Examiner*—Michael Powell Buiz
*Assistant Examiner*—Kevin Truong
*Attorney, Agent, or Firm*—Lyon & Lyon LLP

[57] ABSTRACT

Methods and devices for harvesting blood vessels using balloons to hold the blood vessel and to dissect and mobilize the blood vessel from surrounding tissue. A small balloon catheter is inserted into the blood vessel lumen to and inflated in order to hold the blood vessel, and an everting balloon dissector is everted over the blood vessel. Eversion of the balloon dissector over the blood vessel pushing surrounding body tissue away from the blood vessel.

15 Claims, 7 Drawing Sheets

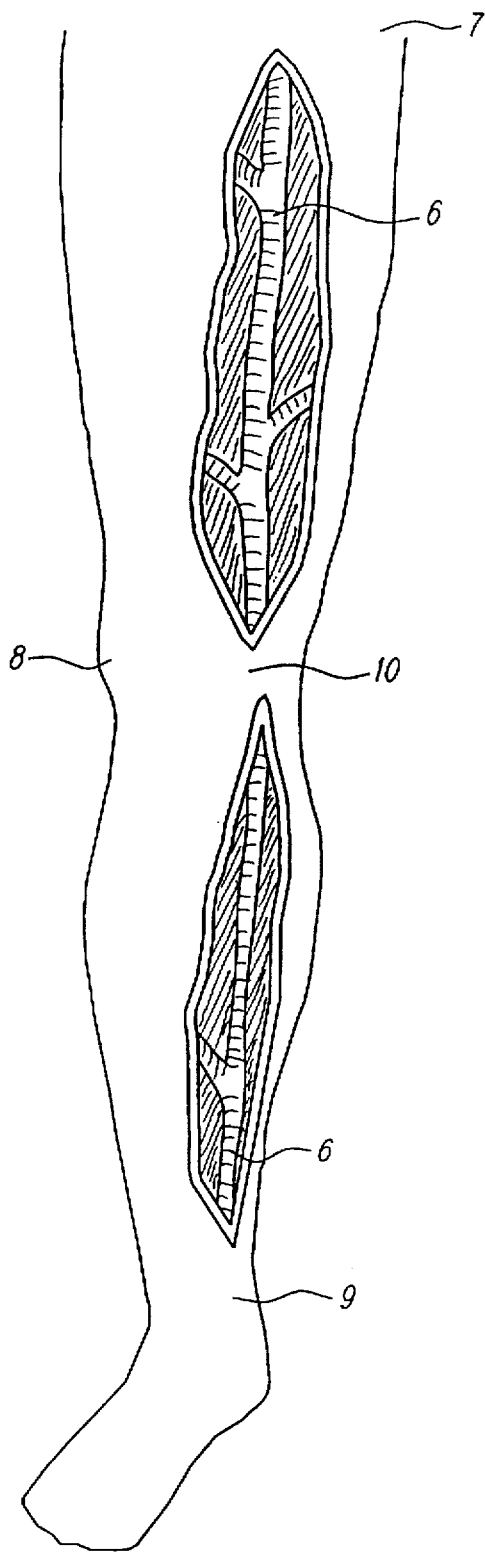
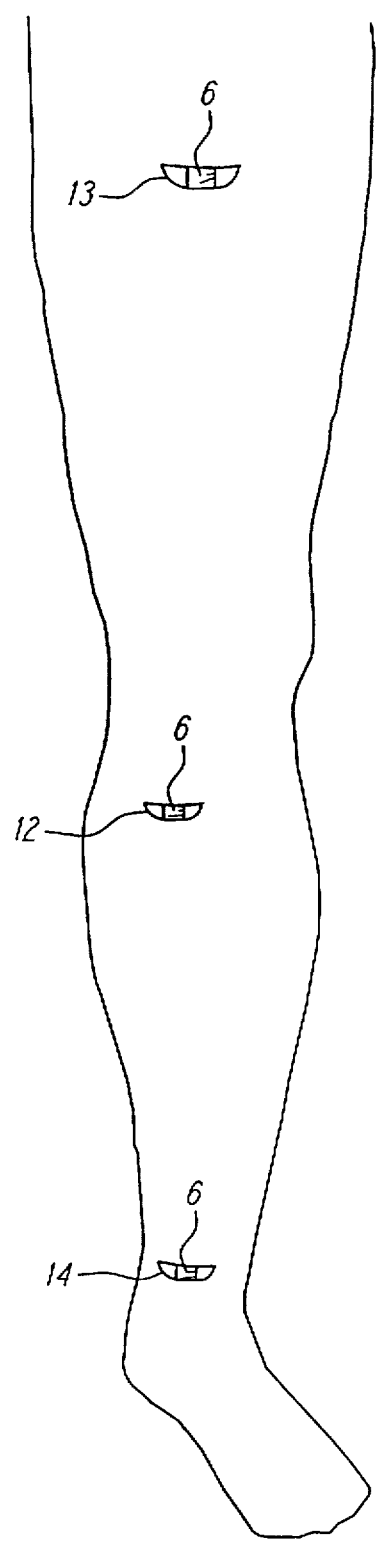
FIG. 2
FIG. 3

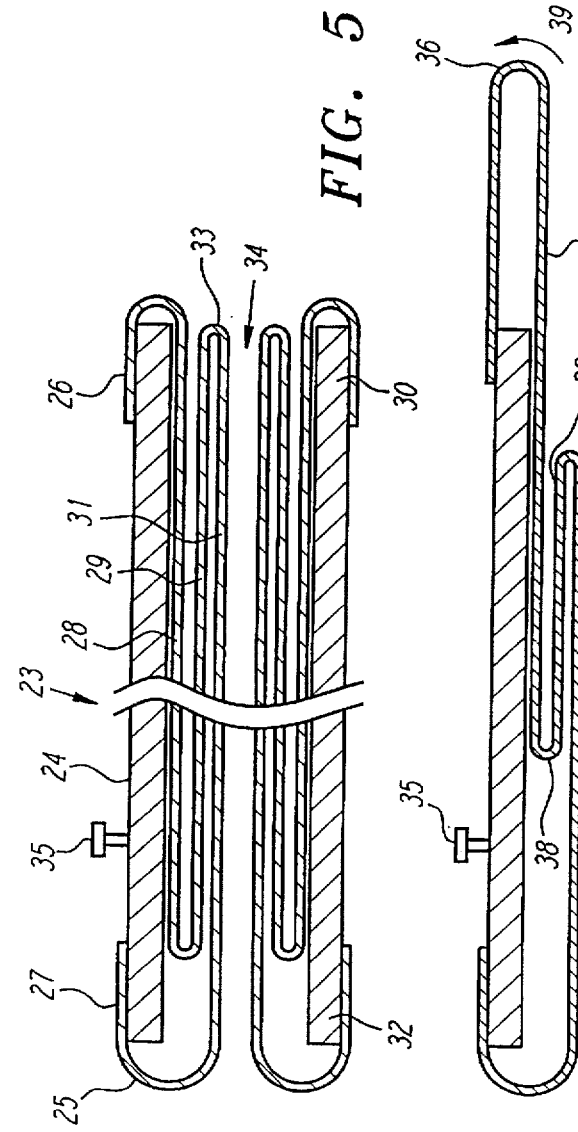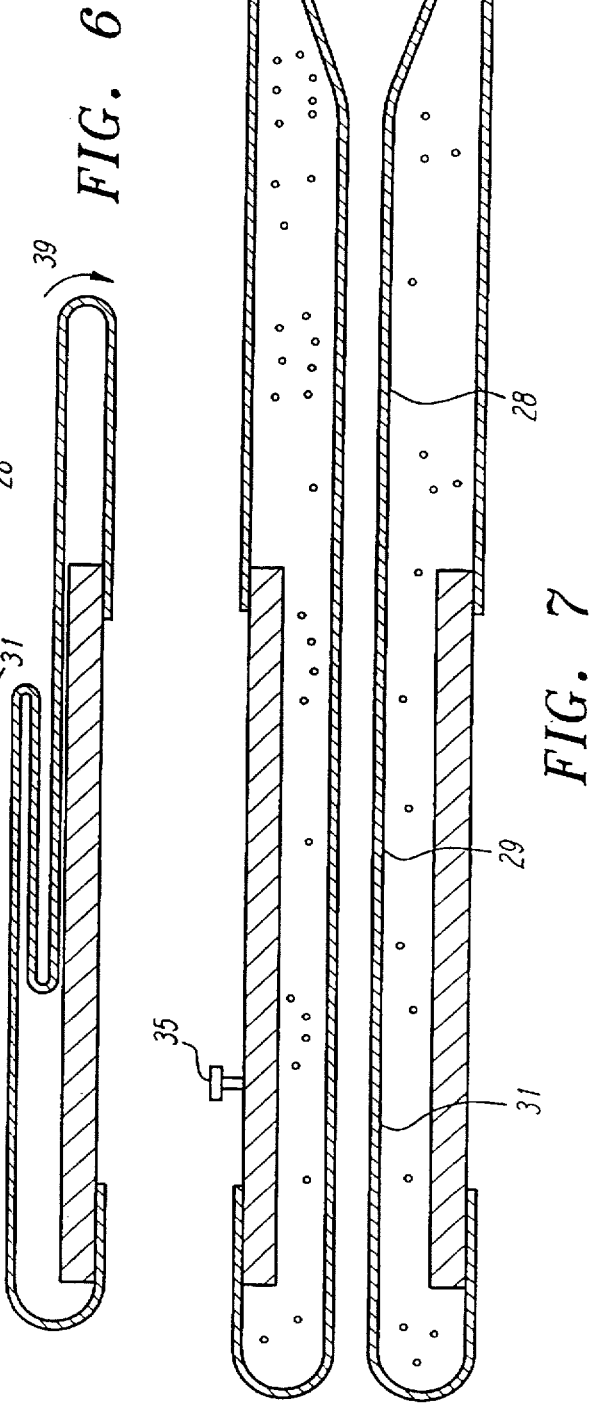

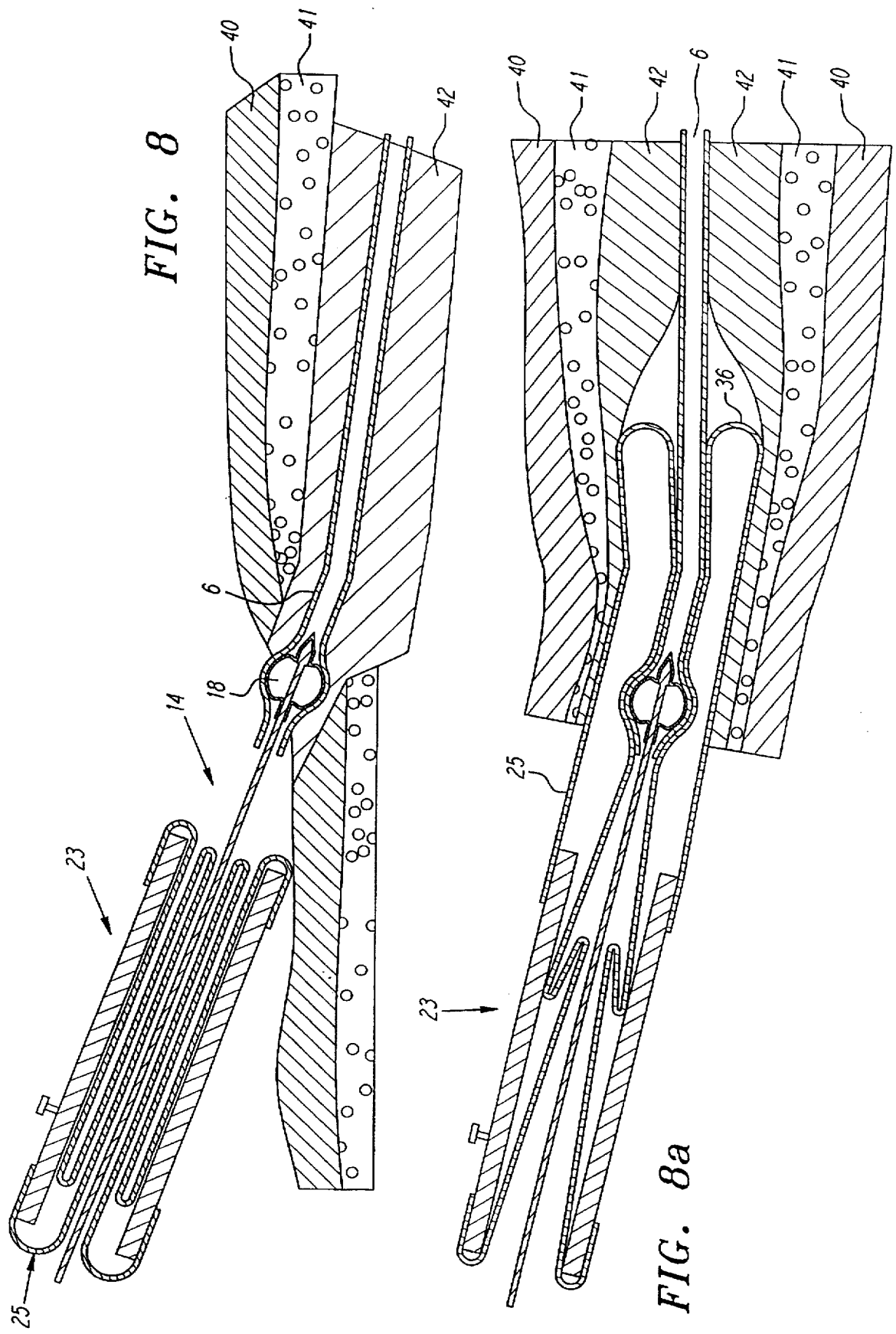

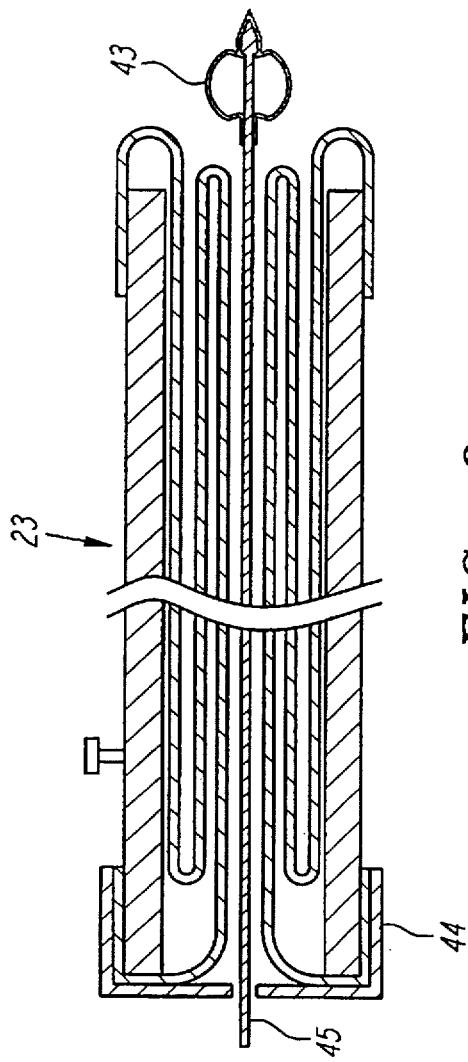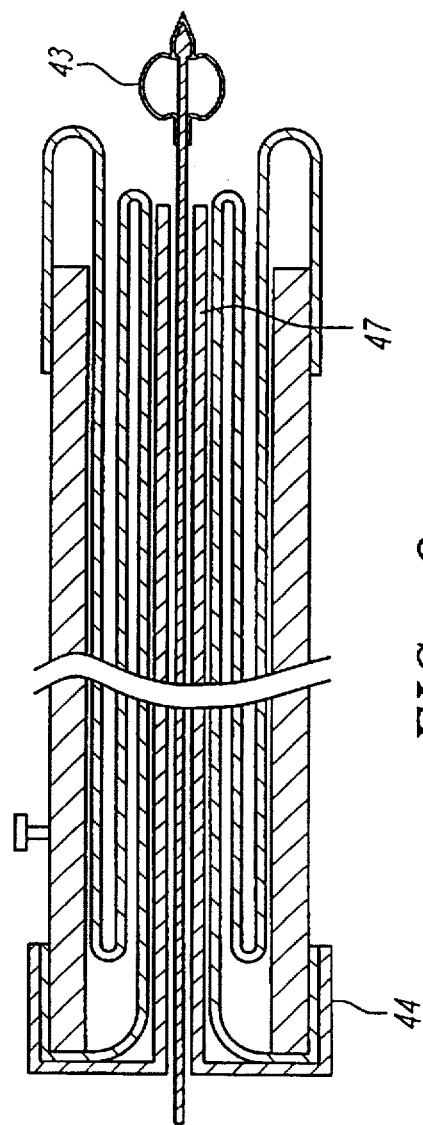

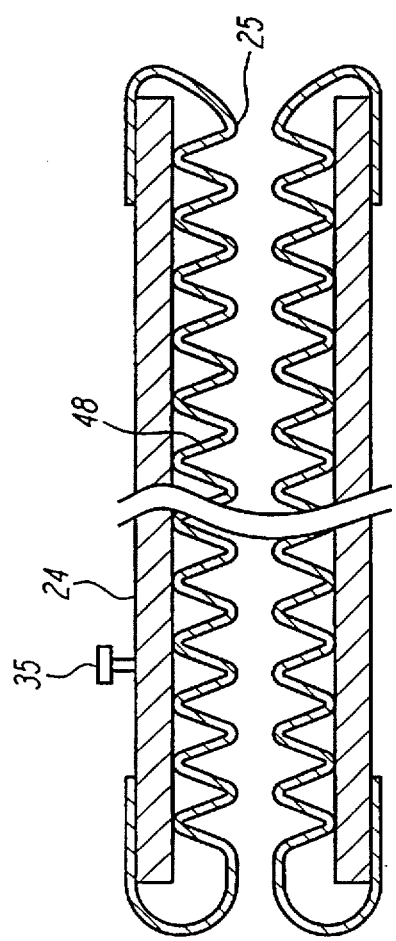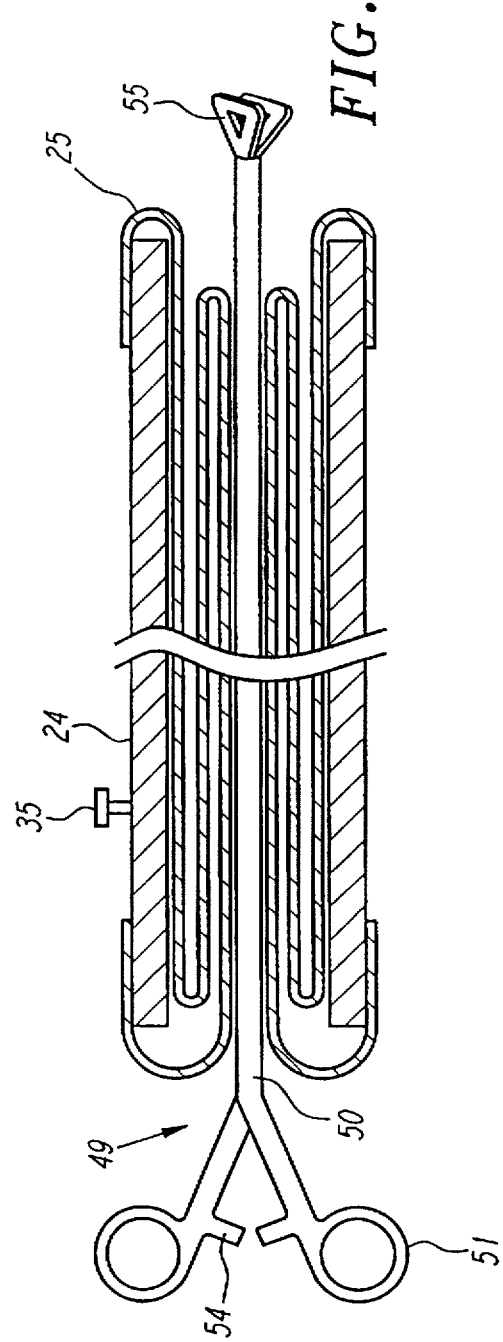

METHODS AND DEVICES FOR HARVESTING BLOOD VESSELS WITH BALLOONS this is a continuation of U.S. application Ser. No. 08/444,426, filed on May 19, 1995 now U.S. Pat. No. 5,593,418, the disclosure of which is hereby incorporated by reference in its entirety. The benefit of the earlier filing date of the aforementioned application is hereby claimed.

FIELD OF THE INVENTION

This invention relates to methods and devices for endoscopic surgery, in particular to methods and devices for dissecting tissue to create a working space for endoscopic instruments.

BACKGROUND OF THE INVENTION

Numerous surgical procedures have been developed to replace arteries that have become blocked by disease. The aortocoronary bypass surgery is perhaps the most important of these bypass operations. The coronary arteries supply blood to the heart. As a result of aging and disease, coronary arteries may become blocked by plaque deposits, stenosis, or cholesterol. In some instances, these blockages can be treated with atherectomy, angioplasty or stent placement, and coronary bypass surgery is not required. Coronary bypass surgery is required when these other methods of treatment cannot be used or have failed to clear the blocked artery. In the coronary bypass surgery, a vein is harvested from elsewhere in the body and grafted into place between the aorta and the coronary artery beyond the point of blockage. An illustration of this surgery is shown in FIG. 1, which shows the heart 1 and the right anterior coronary artery 2 and the left anterior coronary artery 3 which supply blood to the heart. The right anterior coronary artery 2 is blocked in its proximal segment at 2a, as shown. This blockage has been bypassed by grafting a segment of vein 4 between the aorta 5 and the distal segment 2b of the right anterior coronary artery 2. Similarly, the left anterior coronary artery 3 may be blocked, and may require bypass with a length of vein 4a between the aorta and the distal segment 3b of the left anterior artery. The operation requires access to the heart, which means that the chest cavity must be opened completely.

The coronary bypass surgery requires a length of vein or artery for the graft. It is preferred to use a vein taken from the patient undergoing the bypass surgery. The patient is a ready source of suitable veins that will not be rejected by the body after transplantation and grafting onto the aorta and coronary artery. The saphenous vein in the leg is the best substitute for small arteries such as the coronary arteries, and it is the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein, other veins that remain in the leg are adequate to provide adequate return blood flow. The cephalic vein in the arm is an alternative that is sometimes used.

A typical operation previously required to harvest the saphenous vein is illustrated in FIG. 2. The surgeon cuts into the leg to allow access to the saphenous vein and cuts the vein from the leg. To expose the saphenous vein 6, the surgeon makes a series of incisions from the groin 7 to the knee 8 or the ankle 9, leaving one or more skin bridges 10 along the line of the incisions. (Some surgeons make one continuous incision from the groin to the knee or ankle.) Handling of the vein must be kept to a minimum, but the vein must be removed from connective tissue that requires some force to remove. After exposing the vein, the surgeon grasps it with his fingers while stripping off the surrounding tissues with dissecting scissors or other scraping instruments. The surgeon uses his fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lie under the skin-bridges, the surgeon may need to cut one end of the saphenous vein and pull it under the skin bridge to gently pull the vein out from under the skin bridge until the tributary is sufficiently exposed so that it may be ligated and divided when the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can be used to harvest veins for a femoral popliteal bypass, in which an occluded femoral artery is bypassed from the above the occlusion to the popliteal artery above or below the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery. The procedures may be used also to harvest veins for femoral-tibial, femora-peroneal, aorto-femoral, and iliac-femoral by-pass operations and any other by-pass operation.

As can be seen from the description of the harvesting operation, the harvesting operation is very traumatic in its own right. In the case of coronary artery bypass, this operation is carried out immediately before the open chest operation required to graft the harvested vein into the coronary arteries. The vein harvesting operation is often the most troublesome part of the operation. The long incisions created in the leg can be slow to heal and very painful. Complications resulting from the vein harvesting operation can also hinder the patient's recovery from the entire operation.

The method of vein harvesting presented herein is accomplished with endoscopic procedures. This allows the veins to be harvested in an operation that requires only a few small incisions. Endoscopic surgical techniques for operations such as gall bladder removal and hernia repair are now common. The surgeon performing the operation makes a few small incisions and inserts long tools, including forceps, scissors, and staplers, into the incision and deep into the body. Viewing the tools through an endoscope or laparoscope, or a video display from the endoscope, the surgeon can perform all the cutting and suturing operations necessary for a wide variety of operations. The procedures are also referred to as laparoscopic surgery, minimally invasive-surgery or video-assisted surgery. References to endoscopic surgery and endoscopes below is intended to encompass all these fields.

3

Minimally invasive procedures for vein removal have been proposed. Knighton, Endoseope and Method for Vein Removal, U.S. Pat. No. 5,373,840 shows a method of cutting the saphenous vein at one end, and grasping the vein with graspers or forceps, then sliding a ring coaxially over the vein while holding it. Knighton uses a dissecting tool with an annular cutting ring, and requires that the saphenous vein be coaxially overridden or progressively surrounded with the dissecting tool and the endoscope, so that after the endoscope has been inserted as far as it will go, the entire dissected portion of the vein has been pulled into the lumen of the endoscope. AS shown in FIGS. 1 and 10 of Knighton, the method requires deployment the forceps inside the annular dissection loop, and it requires deployment of the loop and graspers inside the endoscope lumen.

The method of vein harvesting presented below uses a balloon to accomplish dissection of the harvested vein. An everted balloon with a central lumen is stored inside a cannula or trocar and is inserted through one of the small incisions and inflated so that it everts out the end of the cannula and forces its way over the vein, thereby separating the vein from surrounding connective tissue.

It is an object of the inventions presented herein to provide methods and devices for harvesting veins with a less traumatic operation than the operations presently used to harvest veins.

SUMMARY OF THE INVENTION

The methods and devices presented herein allow surgeons to harvest veins without making the long incisions previously required, and without the need for pre-tunneling and insufflating a working space over the vein to be harvested. The procedure is a minimally invasive procedure which requires just a single incision at either end of the saphenous vein. The procedure is accomplished with endoscopic or laparoscopic instruments under the guidance of an endoscope. After making the incision, the surgeon mobilizes a short length of the saphenous vein to secure the rolling balloon device to the saphenous vein. The surgeon then inserts the balloon anchor device described below to firmly grip the saphenous vein. The surgeon then inflates the rolling everting balloon dissector described below so that it gradually unfolds over the vein and forces its way between the vein and surrounding connective tissue. The everting balloon will encounter the side branches and its progress over the saphenous vein will be stopped by the side branches. The surgeon will cut the side branches away as they are encountered, using endroscopic clip appliers to ligate the side branches and endoscopic scissors or cutters to divide the side branches.

If desired, the surgeon may create a tunnel by dissecting the fat and skin overlying the saphenous vein away from the vein. The surgeon operating with the vein harvesting device has a choice of tunneling instruments. A typical blunt dissection is performed with a long stiff rod with a round tip, and the tip may be enlarged. The surgeon may also use a device referred to as a peanut, which is long rod with a soft foam tip. Balloons suitable for this purpose are described in co-pending application 08/444,424 entitled Methods and Devices for Blood Vessel Harvesting, incorporated herein by reference. These balloons allow tunneling operation to be accomplished by the balloon, thus allowing easier and less traumatic creation a tunnel over the saphenous vein.

The tunnel may also be insufflated, if desired. When the tunnel has been created, the surgeon seals the tunnel at both ends. The surgeon then injects carbon dioxide into the tunnel at sufficient pressure (typically 5–15 mmHg) to inflate the tunnel and create room for endoscopic instruments. The surgeon then inserts an endoscope through one seal to provide a view of the procedure, and can insert endoscopic cutters and clip appliers. Provision of the working space is optional with the devices and method described below.

With the vein harvester in place, the surgeon inflates the vein harvester to strip the connective tissue from the vein, identify side branches, and remove the vein from its channel in the leg. After the vein is loosened or dissected free from its channel in the leg, the surgeon can cut the second end and easily pull the balloon, which holds the vein, from the leg. The small skin incisions are stitched so they may heal. The small incisions heal much more readily, with fewer complications and far less pain, than the operation now in use.

BRIEF DESCRIPTION OF THE DRAWINGS

FIG. 2 is a view of the leg showing the incisions necessary for harvesting the saphenous vein using currently known methods.

FIGS. 3 is a view of the leg showing the incisions necessary for harvesting the saphenous vein using the methods presented herein.

FIG. 5 is a view of the rolling everting dissecting balloon in its uninflated state.

FIG. 6 is a view of the rolling everting dissecting balloon in its inflated state.

FIG. 7 is a view of the rolling everting dissecting balloon in its fully inflated and everted state.

FIGS. 8 and 8a are cross sections of the rolling everting dissecting balloon in operation over a blood vessel.

FIGS. 9 and 9a are cross sections of a combined anchor device and rolling averting balloon dissector. FIG. 10 shows an alternate embodiment of the everting balloon dissector.

FIG. 11 is a view of a laproscopic gripper being used with the rolling everting balloon dissector.

DETAILED DESCRIPTION OF INVENTION

Figure 1:
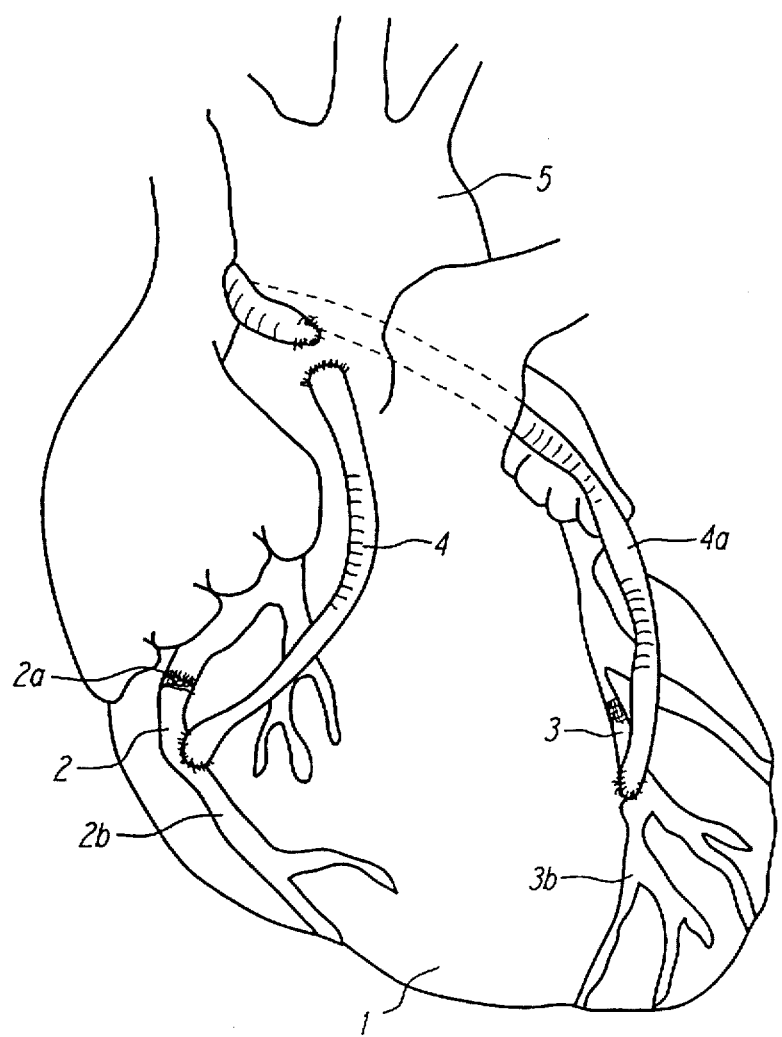
FIG. 1 is a front view of the heart showing a vein grafted from the aorta to the right anterior coronary artery, bypassing the proximal segment of the right anterior coronary artery.

The methods and devices presented herein take advantage of minimally invasive procedures to lesson the trauma of vein harvesting operations. Instead of making an incision over the entire length, or essentially the entire length of the vein to be harvested, the procedure may be conducted with only a single incision. The method may be accomplished with or without creating an insufflated working space over the vein. If a working space is desired, all that is needed is a working space large enough to allow the surgeon to use the endoscopic tools and view the operation through a endoscope. In the preferred embodiment of the method, the surgeon secures the device to the saphenous vein and everts the balloon over the vein. The device creates an adequate working space under the skin and over the saphenous vein at the forward edge of the everting balloon. The surgeon need only make one incision to expose the saphenous vein. These incisions are referred to as cut-downs. Other incisions can be made to facilitate harvesting with the method. For example, a distal incision 12 near the knee and a proximal incision 13 at the groin are preferred if the entire length of the saphenous vein is to be harvested. Where the lower saphenous vein is to be harvested, only an ankle incision 14 is needed to expose the saphenous vein. In FIG. 3, the saphenous vein 6 can be seen through the cut-downs 12, 13 and 14. It will be apparent from the description that the number of incisions used to harvest the entire saphenous vein 6 are merely a matter of convenience and more small incisions may be provided to facilitate use of other devices to be used during related vascular surgery.

Figure 4:
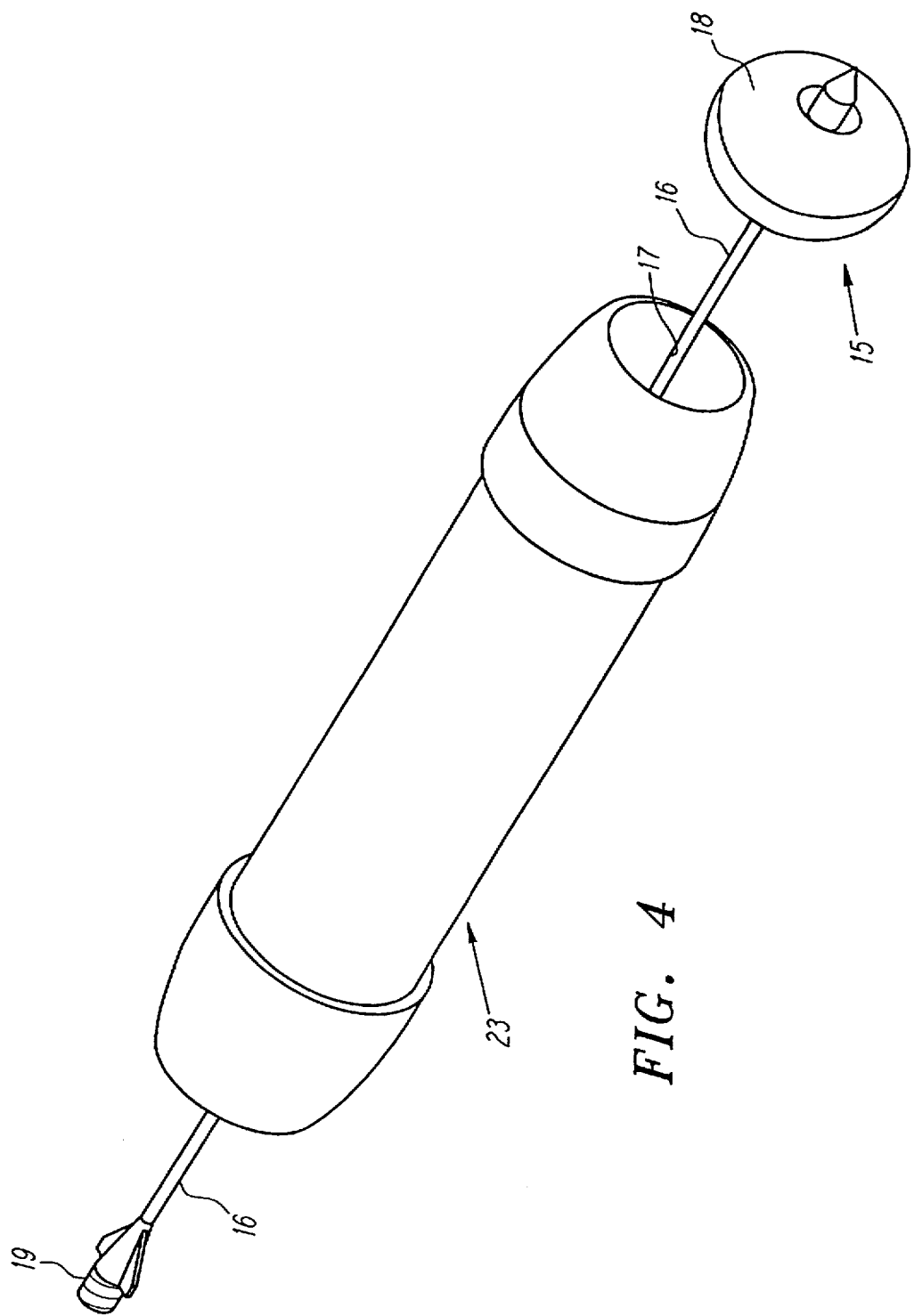
FIG. 4 is a view of a balloon catheter used as an anchor in the procedure disposed within the rolling averting dissecting balloon.

FIG. 4 shows a balloon anchor suitable for use in the method. The anchoring device 15 includes a hollow shaft 16 with an inflation lumen 17 running the length of the shaft to a balloon or inflatable bladder 18 secured to the distal end of the shaft. An inflation fitting 19 is secured to the distal end, and a syringe with plunger and stop cock or valve is screwed onto the inflation fitting. The balloon may be made of latex, silicone rubber, polyethylene, polyimide or other suitable material. FIG. 4 depicts a commercially available 6Fogarty™ Arterial Embolectomy Catheter with a 2cc latex balloon, which is suitable for use in the method, but any available embolectomy, dilatation or angioplasty balloon may be used as an anchor in the method described herein. The balloon anchor has the advantage of securing the mobilized end of the saphenous vein with gentle, uniform compressive force between the anchor balloon and the everting balloon. Also, any expandable device such as a stent catheter, stone basket, Foley catheter, etc. may serve as an anchoring means or anchor device. Also, where it is desirable to take advantage of only those advantageous features of the rolling everting balloon dissector described below, any means of grasping the blood vessel which permits the rolling everting balloon dissector to override the vein may be used. The anchor balloon is shown disposed within the central lumen of everting rolling balloon dissector 23 illustrated in the following figures.

FIG. 5 shows the everting rolling balloon dissector 23 in its uninflated state. A tube or cylinder serves as a balloon housing 24. A long tubular balloon membrane 25, much longer than the balloon housing, is secured to the balloon housing at the distal cuff 26 and the proximal cuff 27. The tubular balloon is first inserted into the balloon housing in coaxial relation, and the cuffs are folded back over the outside of the tube. The balloon is much longer than the balloon housing, and the excess length's double folded inside the balloon housing as shown. The first longitudinal segment 28 remains close to the balloon housing. The second longitudinal segment 29 is pulled back into the center of the tube toward the distal end 30 of the housing. The third longitudinal segment 31 is then pulled back through the central lumen, doubling back inside the second longitudinal segment, toward the proximal end 32 of the housing 24 until it is cuffed over the proximal end of the housing. In this manner, the balloon is folded into one or more radial pleats 33. When folded as shown, the lumen 34 through the center of the tubular balloon is maintained.

FIG. 6 shows the rolling everting balloon partially inflated and partially unfolded or everted. Inflation of the balloon through inflation port 35 forces the balloon to expand. As the balloon in preferably non-elastic, the only way it can expand is to evert or unfold. The leading edge 36 of the balloon constantly advances as the balloon everts and material rolls through the leading edge in the direction shown by the rolling arrows 39. As the first longitudinal segment 28 rolls out of the balloon housing 24, the trailing edge 38 travels forward within the balloon housing and the leading edge travels in the distal direction. FIG. 7 shows the rolling everting balloon in the fully inflated state, where the radial pleats have completely unfolded and the first, second and third longitudinal segments have unfolded to reform the long tubular balloon. The distal end now includes balloon material that was originally at the proximal end.

The use of the rolling everting balloon dissector 23 with the anchor balloon 18 is illustrated in FIG. 8. FIG. 8 shows a divided blood vessel such as the saphenous vein 6 with overlying layers of skin 40 and fat 41 and also covered by typical filmy layer of connective tissue 42. The surgeon prepares the saphenous vein by making an incision near the ankle over the saphenous vein 6. The surgeon inserts the anchoring device 14 through the central lumen of the rolling everting balloon dissector 23. The surgeon then divides the saphenous vein, cutting all the way through it, and mobilizes an inch or two (3 to 6 cm) of the saphenous vein. Then the surgeon inserts the anchor balloon 18 a short distance into the saphenous vein 6 and inflates the anchor balloon until the vein is distended slightly, indicating a tight fit between the anchor balloon and the vein. The surgeon may also choose to ligate the vein just proximal of the anchor balloon, applying a suture or clip around the outside of the vein to lock the balloon in place. After a tight fit is established between the anchor balloon 18 and the vein, the surgeon inflates the rolling everting balloon 25 in the balloon dissector 23, holding it stationary relative to the anchor balloon 18 as illustrated in FIG. 8a, the everting dissecting balloon will force its way over the vein, pushing connective tissue 42 away from the vein and will work its way along the entire length of the vein. In this fashion, the rolling everting balloon will override the saphenous vein and envelop it.

During eversion, the rolling everting dissecting balloon will encounter side branch blood vessels connected to the saphenous vein. When these vessels are encountered, the surgeon can divide and ligate them using endoscopic instruments such as clip appliers and cutters. The endoscopic instruments can be inserted into the leg along the outside of the balloon, through the same incision used to insert the balloon 25, or they can be inserted through the central lumen of the balloon, along that portion of the saphenous vein which has been enveloped by the rolling everting balloon. Presence of a side branch will be evident from resistance to continued eversion of the balloon. After each side branch is divided, the eversion of the balloon can continue until the desired length of vein has been harvested. If a working space has been created over the saphenous vein, the side branches may be ligated with tools inserted through other endoscopic access ports such as the knee incision 12 or groin incision 13 shown in FIG. 3.

FIG. 9 shows a combination device which facilitates use of the anchor balloon 43, rolling everting balloon and endoscopic instruments. The rolling everting balloon dissector 23 is provided with an integral anchor balloon 43. The anchor balloon is mounted on an end cap 44 and shaft 45 which extend a short distance out the distal end of the rolling everting balloon dissector. The shaft is fixed, either permanently with adhesives or integrally formed with the end cap, or it may be tightly engaged in a ring seal provided in the end cap. An inflation tube may be provided to inflate the anchor balloon 43. With the anchor balloon being fixed longitudinally in relation to the dissector by this integral construction, the use of the device is facilitated.

FIG. 9 may be modified to allow for insertion of endoscopes or laparoscopes and instruments through the balloon dissector. Referring to FIG. 9a, by providing a guide tube or cannula 47 extending from the center of the end cap distally into the lumen of the everting balloon and securing the inflation tube 46 to the inside of the cannula, the integrated device can permit endoscopic access through the central lumen while fixing the anchor balloon longitudinally in relation to the dissecting balloon.

A number of different folding patterns may be used to create the rolling everting balloon dissector. While FIGS. 5 through 9 show the radially pleated balloon, FIG. 10 shows an alternate fold. In FIG. 10, the balloon housing 24 and balloon 25 are similar to those shown in FIGS. 5 through 9. The balloon is folded in accordion folds 48, and folded to maintain the central lumen. The accordion folds create longitudinal pleats in the balloon. The term longitudinal pleats indicates that the balloon is folded or pleated along circumferential lines perpendicular to the longitudinal axis of the balloon. Inflation port 35 is aligned to fill the space between the balloon membrane and the balloon housing. When the balloon is inflated, the pressure causes the leading edge to move forward while the accordion pleats unfold. The operation of the accordion folded everting balloon shown in FIG. 10 is similar to the operation of the radially pleated balloon dissector of FIGS. 5 through 9. The longitudinal pleats are preferably deep and numerous, sufficient to allow eversion over the desired length of the saphenous vein or other harvested vein.

Although the method described above has been described using a balloon anchor which is particularly advantageous because it is atraumatic to the vein, any means of grasping the blood vessel which permits the rolling everting balloon dissector to override the vein may be used. Endoscopic graspers and forceps may be used, and the gripping tool of FIG. 11 may replace the anchor balloon when necessary. The gripping tool 49 has an elongated shaft 50 with a handle 51 attached to the proximal end of the shaft 50. The handle is preferably a scissors type handle to actuate the gripping mechanism 55 at the distal end of the shaft 50 and includes a latching mechanism 54 which allows the gripping mechanism to be locked in a set position (e.g., in a gripping position). The shaft 50 transmits the actuating movement from the handle to the gripping mechanism. The gripping mechanism includes a first jaw and a second jaw which oppose each other. The surgeon may use the gripping tool to grip the blood vessel. The jaws of the gripping tool are small enough to fit through the central lumen of the balloon tube so that they may be used in combination with balloon tube as a replacement for the anchor balloon. Conversely, some situations may call for a surgeon to take advantage of the anchor balloon while using other dissectors such as a ring dissector or vein stripper to override the blood vessel while it is grasped atraumatically by the anchor balloon.

The devices and methods described above may be applied to harvesting blood vessels other than the saphenous vein, and may be used for harvesting veins for transplant into any area of the body. The rolling everting balloon dissector may be used for tunneling and dissecting wherever surgeons need to create long working spaces inside the body. The device may be used to create a working space over the vein, as described in co-pending application 08/444,424 before use of the hooked vein harvester described therein. The device may also be used in surgical and non-surgical applications wherever its features prove beneficial. It is specifically contemplated that new materials be applied to the devices and that new methods of folding be applied to the rolling everting balloon dissector.

We claim:

1. A device for enveloping an elongate structure, said device comprising:

a housing having proximal and distal ends; and an elongate balloon disposed on said housing said elongate balloon in its uninflated state being folded, said elongate balloon in its inflated state being at least partially unfolded and forming a tubular shape adapted to envelope the elongate structure, said inflated balloon having a central lumen, said lumen having open distal and proximal ends to allow insertion of a surgical device through said lumen.

2. The device of claim 1 wherein said elongate balloon is made from a nonelastomeric material.

3. The device of claim 1 wherein said elongate balloon in its uninflated state is folded within the tubular member.

4. The device of claim 1 wherein said elongate balloon in its uninflated state is longitudinally and coaxially folded within the housing.

5. The device of claim 1 wherein said elongate balloon in its uninflated state is folded in accordion folds.

6. A device for enveloping an elongate structure, said device comprising:

a housing having proximal and distal ends; and an elongate balloon disposed on said housing, said elongate balloon in its uninflated state being folded, said elongate balloon in its inflated state being at least partially unfolded and forming a tubular shape adapted to envelope the elongate structure, the torodial balloon having a central lumen, said lumen having open distal and proximal ends to allow insertion of a surgical device through said lumen.

7. The device of claim 6 wherein said elongate balloon is made from a nonelastomeric material.

8. The device of claim 6 wherein said elongate balloon in its uninflated state is folded within the housing.

9. The device of claim 6 wherein said elongate balloon in its uninflated state is longitudinally and coaxially folded within the housing.

10. The device of claim 6 wherein said elongate balloon in its uninflated state is folded in accordion folds.

11. A device for separating a vessel in the body from surrounding connected tissue, said device comprising:

a housing having proximal and distal ends; and an elongate balloon disposed on said housing, said elongate balloon in its uninflated state being folded, and said elongate balloon in its inflated state being at least partially unfolded and forming a tubular shape having inner and outer walls, said inner wall defining a lumen, said lumen having open distal and proximal ends to allow insertion of a surgical device through said lumen.

12. The device of claim 11 wherein said elongate balloon is made from a nonelastic material.

13. The device of claim 11 wherein said elongate balloon in its uninflated state is folded within the housing member.

14. The device of claim 11 wherein said elongate balloon in its uninflated state is longitudinally and coaxially folded within the housing.

15. The device of claim 11 wherein said elongate balloon in its uninflated state is folded in accordion folds.

* * * * *

UNITED STATES PATENT AND TRADEMARK OFFICE
CERTIFICATE OF CORRECTION

PATENT NO. : 5,797,947
DATED : August 25, 1998
INVENTOR(S) : Kenneth H. Mollenauer It is certified that error appears in the above-indentified patent and that said Letters Patent is hereby corrected as shown below:

In column 1, line 5, delete "this" and insert therefor –This--.

In column 1, line 6, after "1995" insert ",".

In column 2, line 27, after "from" delete "the".

In column 3, line 2, delete "Endoseope" and insert therefor –Endoscope--.

In column 3, line 12, delete "AS" and insert therefor –As--.

In column 3, line 13, after "deployment" insert "of".

In column 3, line 48, delete "endroscopic" and insert therefor "endoscopic".

In column 3, line 62, after "allow" insert "the".

In column 3, line 64, after "creation" insert "of".

In column 4, line 58, delete "a" and insert therefor "an".

UNITED STATES PATENT AND TRADEMARK OFFICE
CERTIFICATE OF CORRECTION

PATENT NO. : 5,797,947
DATED : August 25, 1998
INVENTOR(S) : Kenneth H. Molleanuer It is certified that error appears in the above-indentified patent and that said Letters Patent is hereby corrected as shown below:

In column 5, line 19, delete "6Fog-" and insert therefor –6F Fogarty™--.

In column 5, line 20, delete "arty™".

In column 5, line 60, delete "in" and insert therefor –is--.

In column 5, line 67, delete "," and insert therefor --.--.

In column 6, line 27, after "18" insert "."; delete "as" and insert therefor "As".

Signed and Sealed this

Twenty-sixth Day of October, 1999

Attest:

Q. TODD DICKINSON

Attesting Officer

Acting Commissioner of Patents and Trademarks